US012727844B2

(12) United States Patent
Cheng

(10) Patent No.: US 12,727,844 B2
(45) Date of Patent: Sep. 8, 2026

(54) SENSING METHOD AND SENSING DEVICE

(71) Applicant: InnoCare Optoelectronics Corporation, Tainan City (TW)

(72) Inventor: Sung-Pao Cheng, Tainan City (TW)

(73) Assignee: InnoCare Optoelectronics Corporation, Tainan City (TW)

( * ) Notice: Subject to any disclaimer, the term of this patent is extended or adjusted under 35 U.S.C. 154(b) by 225 days.

(21) Appl. No.: 18/603,184

(22) Filed: Mar. 12, 2024

(65) Prior Publication Data

US 2024/0358345 A1 Oct. 31, 2024

(30) Foreign Application Priority Data

Apr. 27, 2023 (TW) ................................ 112115733

(51) Int. Cl.
*A61B 6/58* (2024.01)
*G16H 30/20* (2018.01)

(52) U.S. Cl.
CPC ............ *A61B 6/588* (2013.01); *G16H 30/20* (2018.01); *A61B 2562/02* (2013.01)

(58) Field of Classification Search
CPC ..... A61B 6/588; A61B 2562/02; A61B 6/469; A61B 6/08; A61B 6/54; A61B 6/025; A61B 6/06; A61B 6/545; A61B 6/4464; A61B 6/032; A61B 6/589; A61B 6/465; A61B 6/461; A61B 6/587; A61B 6/582; A61B 6/505; A61B 6/4452; A61B 6/463; A61B 6/547; A61B 6/4405; A61B 2090/363; A61B 90/361; A61B 6/04; A61B 6/486; A61B 6/5217; A61B 6/0492; A61B 6/4441; A61B 6/467; A61B 6/0407; A61B 6/44; A61B 6/4208; A61B 6/5211; A61B 6/583; A61B 6/5235; A61B 6/541; A61B 6/50; A61B 6/542; A61B 5/0077; A61B 5/0035; A61B 5/70; A61B 8/54; A61B 5/055; A61B 6/035; A61B 6/548; A61B 6/563; A61B 2560/0266; A61B 5/7267; A61B 5/02055; A61B 5/0004; A61B 5/6889; A61B 5/0033; A61B 8/467; A61B 8/461; A61B 6/56; A61B 6/03; A61B 6/4458; A61B 6/488; A61B 6/544; A61B 6/52; A61B 6/4417; A61B 6/00; A61B 8/00; A61B 6/037; A61B 5/002; A61B 5/14551; A61B 5/7264; A61B 5/743; A61B 5/7275; A61B 2505/03;

(Continued)

(56) References Cited

U.S. PATENT DOCUMENTS 10,482,603 B1 * 11/2019 Fu ........................... G06N 3/09
2011/0064193 A1 * 3/2011 Minnigh ................ A61B 6/505 378/98.12

(Continued)

*Primary Examiner* — Irakli Kiknadze
(74) *Attorney, Agent, or Firm* — JCIPRNET

(57) ABSTRACT

A sensing method and a sensing device are provided. The sensing method includes the following steps: installing the sensing device on a X-ray source device; obtaining a first distance parameter between a X-ray sensing panel and a distance sensor by the distance sensor of the sensing device; obtaining a second distance parameter between a shooting subject and the distance sensor by the distance sensor of the sensing device; and calculating a thickness parameter of the shooting object according to the first distance parameter and the second distance parameter by a microcontroller unit of the sensing device.

18 Claims, 5 Drawing Sheets

(58) Field of Classification Search
CPC ... A61B 5/021; A61B 5/08; A61B 2562/0204; A61B 6/527; A61B 5/11; A61B 6/4435; A61B 5/113; A61B 5/7207; A61B 6/102; A61B 5/704; A61B 2576/00; A61B 5/746; A61B 5/107; A61B 5/1113; A61B 5/6892; A61B 6/0487; A61B 6/481; A61B 8/40; A61B 6/4476; A61B 6/4482; A61B 6/46; G16H 30/20; G16H 40/40; G16H 10/60; G16H 50/50; G16H 30/40; G16H 50/20; G16H 40/67; G16H 40/20; G16H 40/60; G16H 40/63; G16H 50/30; G16H 70/20; G01B 11/06; G01B 11/026; G01S 15/08; G06T 7/74; G06T 2207/30004; G06T 2207/30204; G06T 2207/10116; G06T 7/75; G06T 7/50; G06T 2207/20084; G06T 17/00; G06T 2207/30196; G06T 2207/20081; G06T 2207/10024; G06T 2200/08; G06T 7/70; G06T 7/90; G06T 17/20; G06T 7/0012; G06T 2200/24; G06T 2207/20221; G06T 2207/30168; G06T 2207/30048; G06T 1/0014; G06T 12/10; G06T 2211/404; G06N 3/02; G06N 3/045; G06N 3/09; G06N 3/0464; G06N 3/08; G06N 20/00; G06V 40/20; G06V 10/7796; G06V 10/764; G06V 2201/033; G06V 20/64; G06V 10/774; G06V 10/40; G06V 10/42; G06V 10/82; G06V 40/10; G06V 20/62; G06F 18/2413; G06F 18/21; G06F 18/214; G06F 18/2193; H04N 9/317; A61G 7/10; A61G 2203/36; A61G 2203/44; G08B 3/10
USPC ........................ 378/50, 62, 63, 95, 165, 207
See application file for complete search history.

(56) References Cited

U.S. PATENT DOCUMENTS

| | | | | |
|---|---|---|---|---|
| 2012/0230473 | A1* | 9/2012 | Stagnitto | A61B 6/4291 378/205 |
| 2019/0059829 | A1* | 2/2019 | Han | A61B 6/469 |
| 2020/0289208 | A1* | 9/2020 | Ruff | A61B 90/361 |
| 2022/0030172 | A1* | 1/2022 | Hannemann | A61B 6/0487 |
| 2023/0149114 | A1* | 5/2023 | Boese | A61B 34/10 382/128 |

* cited by examiner

SENSING METHOD AND SENSING DEVICE

CROSS-REFERENCE TO RELATED APPLICATION

This application claims the priority benefit of Taiwan application serial no. 112115733, filed on Apr. 27, 2023. The entirety of the above-mentioned patent application is hereby incorporated by reference herein and made a part of this specification.

BACKGROUND

Technical Field

The disclosure relates to a measurement technology, and particularly relates to a sensing method and a sensing device.

Description of Related Art

Regarding a general X-ray image sensing operation, related setting parameters of an X-ray sensing panel and an X-ray source device need to be manually set by an operator, for example, according to a shooting object and a configuration distance between the X-ray sensing panel and the X-ray source device. Therefore, the general X-ray image sensing operation is likely to have a problem of poor shooting effect due to insufficient information about the shooting object.

SUMMARY

The disclosure provides a sensing method including following steps: installing a sensing device on an X-ray source device; obtaining a first distance parameter between an X-ray sensing panel and a distance sensor by the distance sensor of the sensing device; obtaining a second distance parameter between a shooting object and the distance sensor by the distance sensor of the sensing device; and calculating a thickness parameter of the shooting object according to the first distance parameter and the second distance parameter by a microcontroller unit of the sensing device.

The disclosure provides a sensing device adapted to be installed on an X-ray source device. The X-ray source device is used for irradiating an X-ray sensing panel. The sensing device includes a microcontroller unit and a distance sensor. The distance sensor is coupled to the microcontroller unit and is configured to obtain a first distance parameter between the X-ray sensing panel and the distance sensor, and obtain a second distance parameter between a shooting object and the distance sensor. The microcontroller unit calculates a thickness parameter of the shooting object according to the first distance parameter and the second distance parameter.

Based on the above description, the sensing method and sensing device disclosed in the disclosure are adapted to sense the shooting object placed on the X-ray sensing panel to obtain the thickness parameter of the shooting object, and use the thickness parameter of the shooting object as a setting reference of the X-ray source device.

To make the aforementioned more comprehensible, several embodiments accompanied with drawings are described in detail as follows.

DESCRIPTION OF THE EMBODIMENTS

Figure 1:
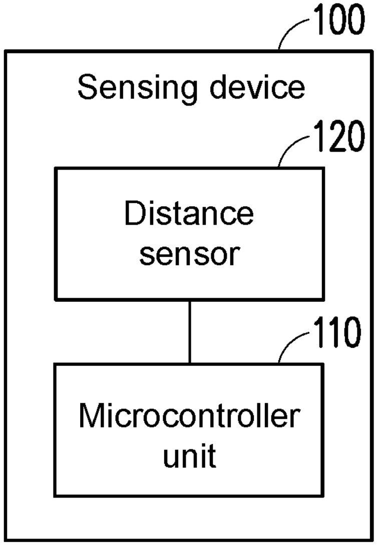
FIG. 1 is a schematic diagram of a sensing device according to an embodiment of the disclosure.

Reference will now be made in detail to the present preferred embodiments of the disclosure, examples of which are illustrated in the accompanying drawings. Wherever possible, the same reference numbers are used in the drawings and the description to refer to the same or like parts. In the following specification and scope of patent application, words such as "comprise" and "include" are open-ended words, so that they should be interpreted as meaning "include but not limited to . . . ".

In the disclosure, terms such as "connect" and "interconnect" related to bonding and connection, unless otherwise specified, may refer to two structures in direct contact, or may also refer to two structures not in direct contact, and there are other structures disposed between these two structures. And the terms about bonding and connection may also include the situation that both structures are movable, or both structures are fixed. In addition, a term "couple" includes any direct or indirect electrical connection means. In the case of direct electrical connection, terminals of components on the two circuits are directly connected or connected to each other through a conductor line segment, while in the case of indirect electrical connection, there are switches, diodes, capacitors, inductors resistors, other suitable elements, or a combination of the above elements between the terminals of the components on the two circuits, but the disclosure is not limited thereto.

It should be noted that, in the following embodiments, without departing from the spirit of the disclosure, features of several different embodiments may be replaced, reorganized, and mixed to complete other embodiments. As long as the features of the various embodiments do not violate or conflict with the spirit of the disclosure, they may be mixed and matched arbitrarily.

FIG. 1 is a schematic diagram of a sensing device according to an embodiment of the disclosure. Referring to FIG. 1, a sensing device 100 includes a microcontroller unit (MCU) 110 and a distance sensor 120. The microcontroller unit 110 is coupled to the distance sensor 120. In the embodiment, the sensing device 100 is adapted to be installed on an X-ray source device, and the X-ray source device is configured to irradiate (illuminate) toward an X-ray sensing panel. In this regard, before performing an X-ray sensing operation, the sensing device 100 may first perform a sensing operation to obtain relevant sensing parameters related to a shooting object or shooting environment, so that a computing device or a user (such as a radiologist) may accordingly set the X-ray source device according to relevant sensing parameters.

In the embodiment, the sensing device 100 may be, for example, implemented as a detachable component for being installed on the X-ray source device. Specifically, the sensing device 100 may be installed on the X-ray source device through magnetic attraction. In this regard, when the sensing device 100 is installed on the X-ray source device, the sensing device 100 may be magnetically adsorbed on the X-ray source device through a magnet element of the sensing device 100, and is adjacent to a position of a light source, so as to accurately sense related distance parameters. In an embodiment, the sensing device 100 may also be mounted on the X-ray source device through, for example, a specially designed mechanism or mechanical element. In addition, the shooting object mentioned in the disclosure may refer to a certain part, organ or viscera of a human body, but the disclosure is not limited thereto.

In the embodiment, the microcontroller unit 110 may include a central processing unit (CPU) (or other computing circuits) and a memory, and may have a parameter and/or image computing function. In the embodiment, the distance sensor 120 may be, for example, an infrared (IR) distance sensor, an ultrasonic distance sensor, a laser distance sensor, an optical distance sensor or an electromagnetic distance sensor, etc., which is not limited by the disclosure.

Figure 2:
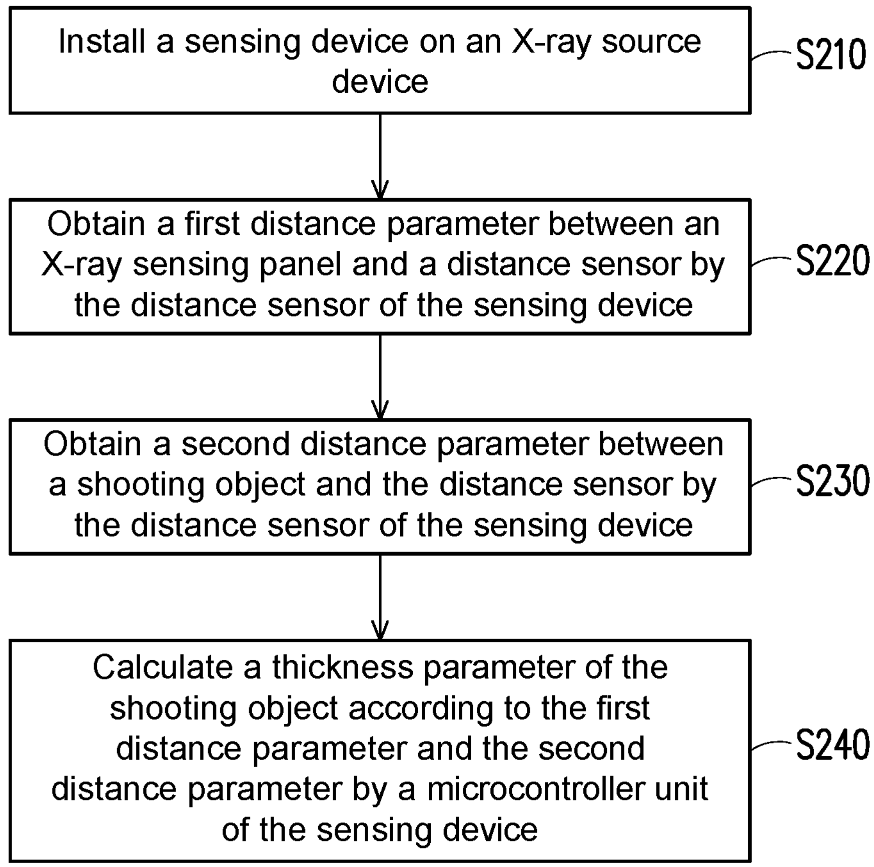
FIG. 2 is a flowchart of a sensing method according to an embodiment of the disclosure.
Figure 3B:
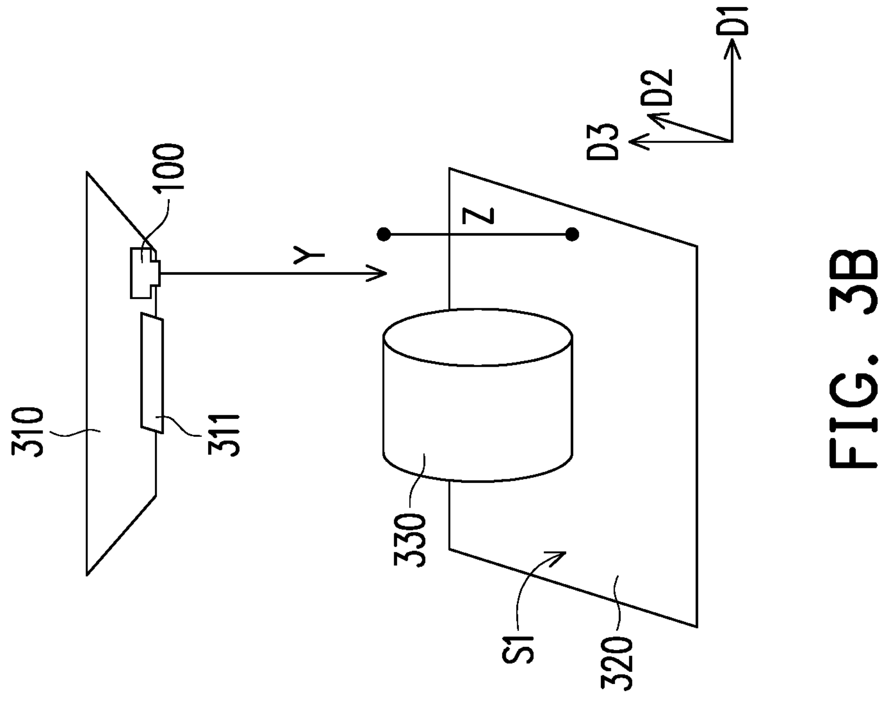
FIG. 3A and FIG. 3B are schematic diagrams of a sensing operation according to an embodiment of the disclosure.
Figure 3A:
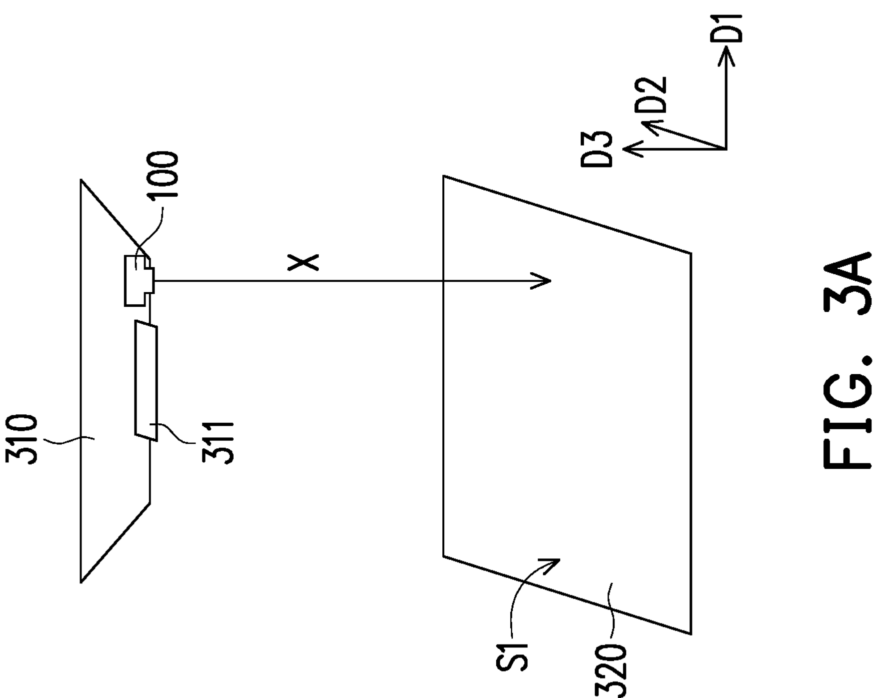

FIG. 2 is a flowchart of a sensing method according to an embodiment of the disclosure FIG. 3A and FIG. 3B are schematic diagrams of a sensing operation according to an embodiment of the disclosure. Referring to FIG. 1 to FIG. 3B, the sensing device 100 may perform following steps S210-S240 to implement X-ray image shooting. In step S210, the sensing device 100 may be installed on an X-ray source device 310. As shown in FIG. 3A, a sensing surface S1 of an X-ray sensing panel 320 may be parallel to a plane extending in a direction D1 (horizontal direction) and a direction D2 (horizontal direction). The X-ray source device 310 may be disposed above the X-ray sensing panel 320 along a direction D3 (vertical direction). The direction D1, the direction D2 and the direction D3 are perpendicular to each other. A light emitting path of a light emitting source 311 (i.e. an X-ray tube) of the X-ray source device 310 may be directed toward the X-ray sensing panel 320. The sensing device 100 may be installed on the X-ray source device 310 and may be located adjacent to a position of the light emitting source 311 of the X-ray source device 310. A sensing path of the distance sensor 120 may be, for example, parallel to the light emitting path of the light emitting source 311.

In step S220, the distance sensor 120 of the sensing device 100 may obtain a first distance parameter X between the X-ray sensing panel 320 and the distance sensor 120. As shown in FIG. 3A, before shooting, the sensing device 100 may perform distance sensing through the distance sensor 120 in advance in a situation where there is no shooting object, so as to obtain the first distance parameter X, and the microcontroller unit 110 stores the first distance parameter X.

In step S230, the distance sensor 120 of the sensing device 100 may obtain a second distance parameter Y between the shooting object 330 and the distance sensor 120. As shown in FIG. 3B, before shooting, a user may place the shooting object 330 on the sensing surface S1 of the X-ray sensing panel 320, and the sensing device 100 may perform distance sensing on the shooting object 330 through the distance sensor 120 to obtain the second distance parameter Y, and the microcontroller unit 110 stores the second distance parameter Y.

In step S240, the microcontroller unit 110 of the sensing device 100 may calculate a thickness parameter Z of the shooting object 330 according to the first distance parameter X and the second distance parameter Y. In the embodiment, the microcontroller 110 unit may perform parameter calculation to subtract the second distance parameter Y from the first distance parameter X to obtain the thickness parameter Z of the shooting object 330. The microcontroller unit 110 may display the thickness parameter Z through a display device. The thickness parameter Z may represent a distance of the light emitting path of the light emitting source 311 passing through the shooting object 330. Therefore, the user may adjust setting parameters of the X-ray source device 310 and/or the X-ray sensing panel 320 according to the thickness parameter Z of the shooting object 330, so as to adaptively adjust related settings of the X-ray source device 310 and the X-ray sensing panel 320 according to thickness parameters of different shooting objects.

In an embodiment, the microcontroller unit 110 may output the thickness parameter Z to the computing device. Even, the computing device may further automatically adjust, calculate or obtain the setting parameters of the X-ray source device 310 and/or the X-ray sensing panel 320 according to the thickness parameter Z. In the regard, the computing device may be an external computer device, or the computing device may also be set in the sensing device. In addition, in another embodiment, the sensing device 100 may output at least one of the first distance parameter X, the second distance parameter Y, and the thickness parameter Z to the computing device, but the disclosure is not limited to the above.

Figure 4:
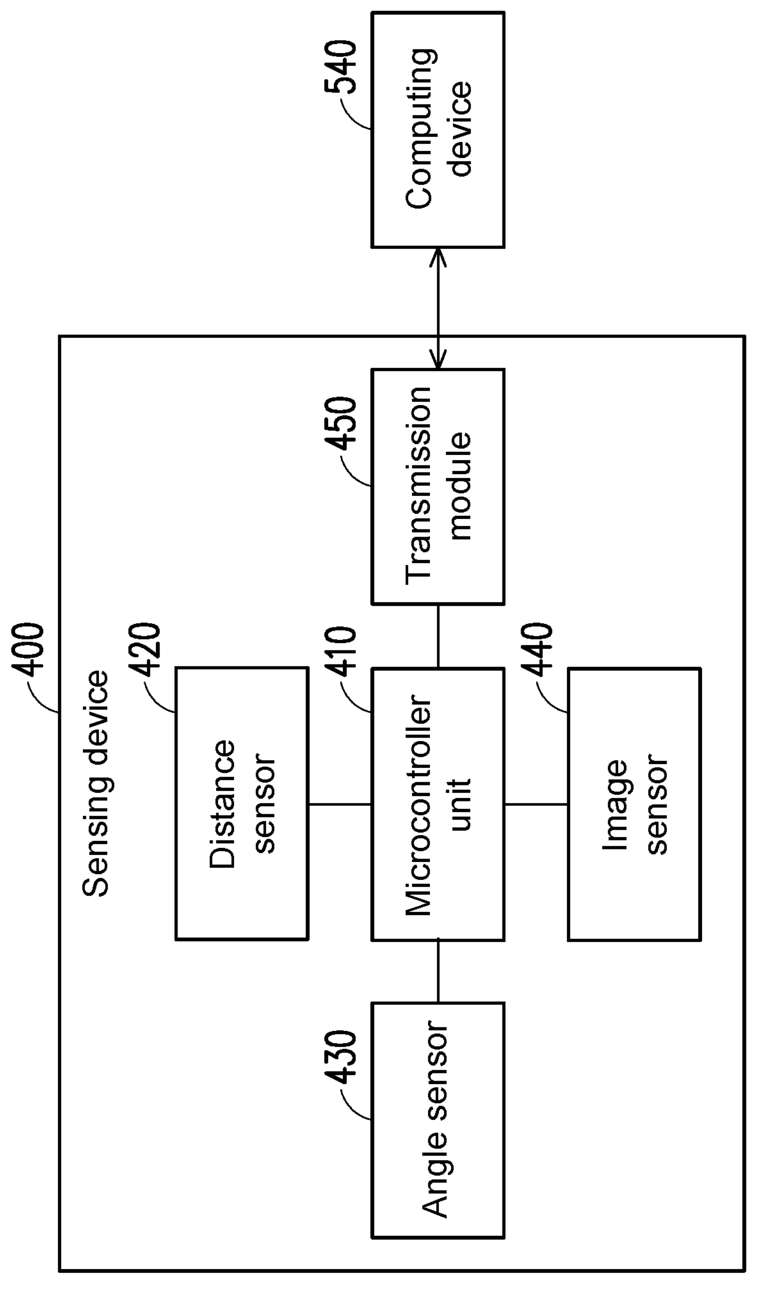
FIG. 4 is a schematic diagram of a sensing device according to another embodiment of the disclosure.

FIG. 4 is a schematic diagram of a sensing device according to another embodiment of the disclosure. Referring to FIG. 4, the sensing device 400 includes a microcontroller unit 410, a distance sensor 420, an angle sensor 430, an image sensor 440 and a transmission module 450. The microcontroller unit 410 is coupled to the distance sensor 420, the angle sensor 430, the image sensor 440 and the transmission module 450. The transmission module 450 may communicate with a computing device 540 and transmit related parameters and/or image data to the computing device 540. The computing device 540 may be an external computer device, or the computing device 540 may also be a computing device provided in the sensing device.

In the embodiment, for related technical content of the microcontroller unit 410 and the distance sensor 420, reference may be made to the description of the microcontroller unit 110 and the distance sensor 120 in the above-mentioned embodiment, and details thereof are not repeated here. In the embodiment, the angle sensor 430 may be, for example, a rotary potentiometer, an optical encoder, and a magnetic rotary encoder. In the embodiment, the image sensor 440 may be, for example, a charge coupled device (CCD) image sensor or a complementary metal-oxide-semiconductor (CMOS) image sensor. In the embodiment, the transmission module 450 may be, for example, a wireless communication module or a wired communication module. The wireless communication module may be, for example, a Bluetooth module or a WiFi module. The wired communication module may be, for example, connected to the computing device 540 through a cable. The transmission module 450 may include a transmission interface and a signal processing circuit.

Figure 5B:
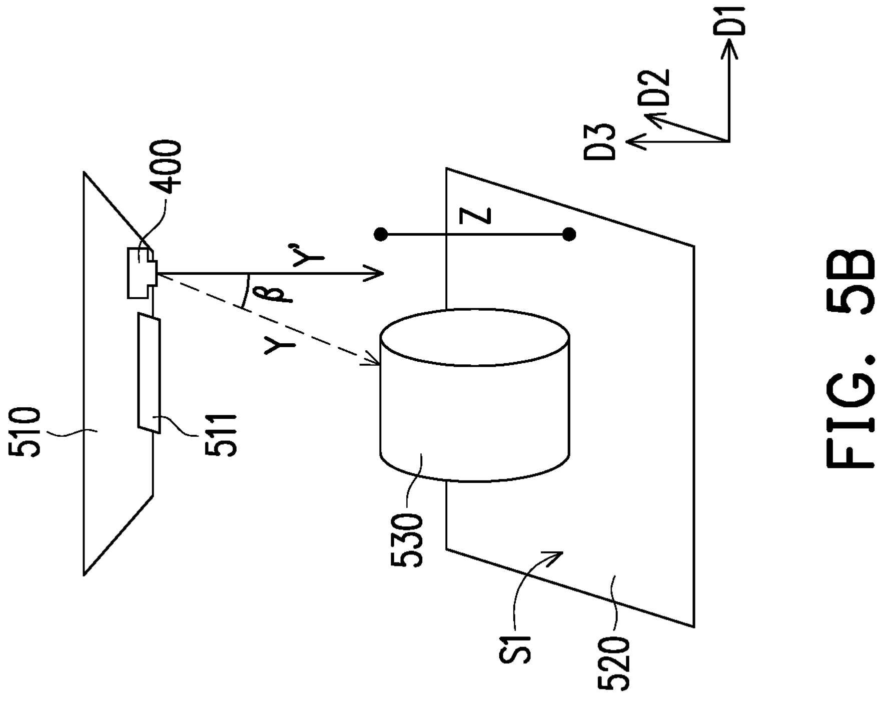
FIG. 5A and FIG. 5B are schematic diagrams of a sensing operation according to another embodiment of the disclosure.
Figure 5A:
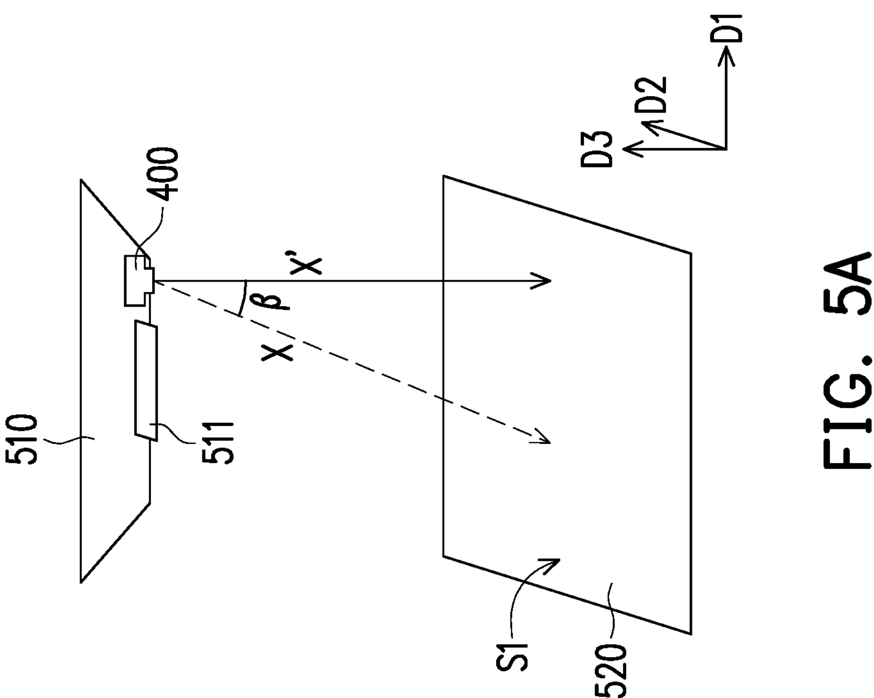

FIG. 5A and FIG. 5B are schematic diagrams of a sensing operation according to another embodiment of the disclosure. Referring to FIG. 4 to FIG. 5B, the sensing device 400 may be mounted on an X-ray source device 510. As shown in FIG. 5A, a sensing surface S1 of an X-ray sensing panel 520 may be parallel to a plane respectively extending in the direction D1 (horizontal direction) and the direction D2 (horizontal direction). The X-ray source device 510 may be disposed above the X-ray sensing panel 520 along the direction D3 (vertical direction). A light emitting path of a light emitting source 511 of the X-ray source device 510 may be directed toward the X-ray sensing panel 520. The sensing device 400 may be installed on the X-ray source device 510 and may be located adjacent to a position of the light emitting source 511 of the X-ray source device 510. It should be noted that for the related technical content of the sensing device 400 in the embodiment, reference may also be made to the description of the sensing device 100 in the above-mentioned embodiment, and detail thereof will not be repeated here.

As shown in FIG. 5A, before shooting, in the situation where a shooting object 530 is not placed on the X-ray sensing panel 520, the distance sensor 420 of the sensing device 400 may obtain the first distance parameter X between the X-ray sensing panel 520 and the distance sensors 420. The microcontroller unit 410 may store the first distance parameter X. Then, the angle sensor 430 of the sensing device 400 may obtain a tilt angle parameter β, and the microcontroller unit 410 may store the tilt angle parameter β. The microcontroller unit 410 may correct the first distance parameter X according to the tilt angle parameter β, and store a corrected first distance parameter X'.

As shown in FIG. 5B, before shooting, in the situation where an object 530 is placed on the X-ray sensing panel 520, the distance sensor 420 of the sensing device 400 may obtain the second distance parameter Y between the shooting object 530 and the distance sensor 420. The microcontroller unit 410 may store the second distance parameter Y. Then, the microcontroller unit 410 may read the tilt angle parameter β stored in the previous sensing, or the angle sensor 430 of the sensing device 400 may obtain a new tilt angle parameter again. The microcontroller unit 410 may correct the second distance parameter Y according to the tilt angle parameter β or the new tilt angle parameter, and store a corrected second distance parameter Y'.

In other words, if the X-ray source device 510 or the sensing device 400 is not parallel to the sensing surface S1 of the X-ray sensing panel 520 (i.e., the sensing path of the distance sensor 420 is not perpendicular to the sensing surface S1 of the X-ray sensing panel 520, and has a tilt angle with a normal line of the sensing surface S1) to cause errors in the first distance parameter X and the second distance parameter Y respectively, the microcontroller unit 410 may automatically correct the first distance parameter X and the second distance parameter Y to generate the corrected first distance parameter X' and the corrected second distance parameter Y'. Moreover, the microcontroller unit 410 may calculate the thickness parameter Z of the shooting object 530 according to the corrected first distance parameter X' and the corrected second distance parameter Y'. In the embodiment, the microcontroller 410 may perform parameter calculation to subtract the corrected second distance parameter Y' from the corrected first distance parameter X' to obtain the thickness parameter Z of the shooting object 530.

Moreover, the sensing device 400 may also obtain a sensing image of the shooting object 530 through the image sensor 440, and provide the thickness parameter Z and the sensing image to the computing device 540 through the transmission module 450 of the sensing device 400. In the embodiment, the computing device 540 may further execute an artificial intelligence (AI) module or other image identification modules to identify a shooting object image in the sensing image to obtain object type information of the shooting object 530.

In the embodiment, the computing device 540 may display the thickness parameter Z and the object type information through a display device. Therefore, the user may accordingly adjust the setting parameters of the X-ray source device 510 and/or the X-ray sensing panel 520 according to the thickness parameter Z and the object type information of the shooting object 530, so as to adaptively adjust related settings of the X-ray source device 510 and/or the X-ray sensing panel 520 according to object types and thickness parameters of different shooting objects. In an embodiment, the computing device 540 may also automatically perform correlation calculations according to the object type information and the thickness parameter Z, so as to obtain the setting parameters of the X-ray source device 510 and/or the X-ray sensing panel 520.

For example, referring to following table 1, taking a hand, an abdomen and a chest of a human body as an example, if the body part is the hand, suitable energy of an X-ray beam emitted by the light emitting source 511 of the X-ray source device 510 may be 45 kilovolts peaks (kVp), a suitable intensity of the X-ray beam may be 2 milliamps per second (mAs), and a suitable focal spot to image receptor distance (SID) between the light emitting source 511 and the X-ray sensing panel 520 may be 110 centimeters (cm). If the body part is the abdomen, the suitable energy of the X-ray beam emitted by the light emitting source 511 of the X-ray source device 510 may be 75 kilovolts peaks, the suitable intensity of the X-ray beam may be 25 milliamps per second, and the suitable SID between the light emitting source 511 and the X-ray sensing panel 520 may be 110 cm. If the body part is the chest, the suitable energy of the X-ray beam emitted by the light emitting source 511 of the X-ray source device 510 may be 110 kilovolts peaks, the suitable intensity of the X-ray beam may be 4 milliamps per second, and the suitable SID between the light emitting source 511 and the X-ray sensing panel 520 may be 180 cm. Namely, the user or the computing device 540 may obtain the suitable energy, suitable intensity and SID of the X-ray beam according to the information in Table 1 below, and accordingly the user or the computing device 540 may accordingly adjust the energy, intensity of the X-ray source device 510 and/or the distance between the light emitting source 511 of the X-ray source device 510 and the X-ray sensing panel 520 to achieve a good X-ray image shooting effect.

TABLE 1

| Body part | Energy (kVp) | Intensity (mAs) | SID (cm) |
|---|---|---|---|
| Hand | 45 | 2 | 110 |
| Abdomen | 75 | 25 | 110 |
| Chest | 110 | 4 | 180 |

In an embodiment, the computing device 540 may further identify the sensing image and obtain object size information of the shooting object 530. In this way, the user may correspondingly adjust the setting parameters of the X-ray source device 510 and/or the X-ray sensing panel 520 according to the thickness parameter Z, the object type information, and the object size information of the shooting object 530.

In an embodiment, the sensing image may include a shooting object image and a background image. In this regard, as shown in FIG. 5A, in the situation where no shooting object 530 is placed on the X-ray sensing panel 520, the sensing device 400 may first obtain the background image of the X-ray sensing panel 520 (i.e., only the image of the sensing surface S1 of the X-ray sensing panel 520) through the image sensor 440. The microcontroller unit 410 may provide the background image to the computing device 540 through the transmission module 450. In this way, the computing device 540 may perform background removal processing on the sensing image according to the background image, so as to obtain a background-removed sensing image. Then, the computing device 540 may input the background-removed sensing image to the artificial intelligence module to identify the sensing image and obtain the object type information of the shooting object 530. In other words, a calculation amount for the computing device 540 to identify the sensing image may be effectively reduced. In addition, it should be noted that, in another embodiment, the microcontroller unit 410 may also directly perform background removal processing on the sensing image, and provide the background-removed sensing image to the computing device 540 through the transmission module 450.

In an embodiment, the sensing device 400 may further include a battery module, where the battery module may include a power management module and a storage battery. The microcontroller unit 410 may be coupled to the power management module, and the power management module may be coupled to the storage battery. In this way, the sensing device 400 may be conveniently installed on the X-ray source device 510 to perform the aforementioned sensing operation without external power supply. Moreover, in another embodiment, the sensing device 400 may also be realized in an appearance of the battery module, so as to be suitable for being accommodated in the X-ray sensing panel 520. Even, when the sensing device 400 is accommodated in the X-ray sensing panel 520, the battery module of the sensing device 400 may obtain a charging signal from the X-ray sensing panel 520. In this way, the sensing device 400 and the X-ray sensing panel 520 may be portable, and may effectively increase a usage time of the sensing device 400.

In summary, the sensing method and sensing device disclosed in the disclosure may effectively sense the thickness parameter of the shooting object. Moreover, in some embodiments, the sensing method and sensing device of the disclosure may also obtain the sensing image of the shooting object to identify the object type information and/or object size information of the shooting object. In this way, related settings of the X-ray source device and the X-ray sensing panel may be adaptively adjusted according to the above parameters to achieve a good shooting effect.

It will be apparent to those skilled in the art that various modifications and variations can be made to the disclosed embodiments without departing from the scope or spirit of the disclosure. In view of the foregoing, it is intended that the disclosure covers modifications and variations provided they fall within the scope of the following claims and their equivalents.

What is claimed is:

1. A sensing method, comprising:
- installing a sensing device on an X-ray source device;
- obtaining a first distance parameter between an X-ray sensing panel and a distance sensor by the distance sensor of the sensing device;
- obtaining a second distance parameter between a shooting object and the distance sensor by the distance sensor of the sensing device;
- obtaining a tilt angle parameter by an angle sensor of the sensing device;
- correcting the first distance parameter and the second distance parameter by a microcontroller unit of the sensing device according to the tilt angle parameter; and
- calculating a thickness parameter of the shooting object according to the corrected first distance parameter and the corrected second distance parameter by the microcontroller unit of the sensing device.

2. The sensing method as claimed in claim 1, further comprising:
- providing the thickness parameter to a computing device through a transmission module of the sensing device.

3. The sensing method as claimed in claim 2, further comprising:
- obtaining a setting parameter of the X-ray source device by the computing device according to the thickness parameter.

4. The sensing method as claimed in claim 2, further comprising:
- obtaining a sensing image of the shooting object by an image sensor of the sensing device; and
- providing the thickness parameter and the sensing image to the computing device through the transmission module of the sensing device.

5. The sensing method as claimed in claim 4, further comprising:
- executing an artificial intelligence module by the computing device to identify the sensing image and obtain object type information of the shooting object.

6. The sensing method as claimed in claim 5, further comprising:
- obtaining a setting parameter of the X-ray source device by the computing device according to the object type information and the thickness parameter.

7. The sensing method as claimed in claim 4, further comprising:
- identifying the sensing image by the computing device, and obtaining object size information of the shooting object.

8. The sensing method as claimed in claim 4, further comprising:
- obtaining a background image of the X-ray sensing panel by an image sensor; and
- providing the background image to the computing device through the transmission module.

9. The sensing method as claimed in claim 8, further comprising:
- performing a background removal processing on the sensing image by the computing device according to the background image.

10. The sensing method as claimed in claim 2, wherein the computing device is an external computer device.

11. The sensing method as claimed in claim 2, wherein the computing device is set in the sensing device.

12. The sensing method as claimed in claim 1, wherein the sensing device is further configured to be accommodated in the X-ray sensing panel.

13. The sensing method as claimed in claim 12, further comprising:
- obtaining a charging signal from the X-ray sensing panel by a battery module of the sensing device when the sensing device is accommodated in the X-ray sensing panel.

14. The sensing method as claimed in claim 1, further comprising:
- magnetically attracting the sensing device to the X-ray source device by a magnet element of the sensing device when the sensing device is installed on the X-ray source device.

15. A sensing device, configured to be installed on an X-ray source device, the X-ray source device being configured to irradiate an X-ray sensing panel, and the sensing device comprising:

a microcontroller unit;

a distance sensor, coupled to the microcontroller unit and configured to obtain a first distance parameter between the X-ray sensing panel and the distance sensor, and obtain a second distance parameter between a shooting object and the distance sensor; and an angle sensor, coupled to the microcontroller unit, and configured to obtain a tilt angle parameter, wherein the microcontroller unit corrects the first distance parameter and the second distance parameter according to the tilt angle parameter, and calculates a thickness parameter of the shooting object according to the corrected first distance parameter and the corrected second distance parameter.

16. The sensing device as claimed in claim 15, further comprising:

a transmission module, coupled to the microcontroller unit, and configured to connect with a computing device, wherein the microcontroller unit provides the thickness parameter to the computing device through the transmission module.

17. The sensing device as claimed in claim 15, further comprising:

an image sensor, coupled to the microcontroller unit, and configured to obtain a sensing image of the shooting subject, and a transmission module, coupled to the microcontroller unit, and configured to connect with a computing device, wherein the microcontroller unit provides the thickness parameter and the sensing image to the computing device through the transmission module.

18. The sensing device as claimed in claim 17, wherein the image sensor is configured to obtain a background image of the X-ray sensing panel, and the microcontroller unit provides the background image to the computing device through the transmission module.

* * * * *